United States Patent [19]
Goddard et al.

[11] Patent Number: 5,992,158
[45] Date of Patent: Nov. 30, 1999

[54] CRYOSURGICAL INSTRUMENT

[75] Inventors: Robert William Goddard; Leslie John Penny, both of Andover, United Kingdom

[73] Assignee: Spembly Medical Limited, Andover, United Kingdom

[21] Appl. No.: 08/873,138

[22] Filed: Jun. 9, 1997

Related U.S. Application Data

[63] Continuation of application No. PCT/GB95/00739, Mar. 31, 1995.

[51] Int. Cl.[6] ........................................ F25B 19/02
[52] U.S. Cl. ............................ 62/51.2; 62/50.7; 62/293; 606/24; 606/25
[58] Field of Search .................. 62/51.2, 50.7, 62/293; 606/24, 25

[56] References Cited

U.S. PATENT DOCUMENTS

| | | | |
|---|---|---|---|
| 3,257,823 | 6/1966 | Hogan | 62/51.2 |
| 3,667,248 | 6/1972 | Carlson | 62/293 |
| 3,696,813 | 10/1972 | Wallach | 62/293 |
| 3,971,383 | 7/1976 | van Gerver | 606/23 |
| 4,107,946 | 8/1978 | Potter | 62/50.7 |
| 5,254,116 | 10/1993 | Baust et al. | 606/23 |
| 5,452,582 | 9/1995 | Longsworth | 62/293 |
| 5,520,682 | 5/1996 | Baust et al. | 62/293 |
| 5,540,062 | 7/1996 | Maytal | 62/293 |

FOREIGN PATENT DOCUMENTS

| | | |
|---|---|---|
| 0 584 930 A1 | 2/1994 | European Pat. Off. . |
| 0 655 225 A1 | 5/1995 | European Pat. Off. . |
| WO 93/04647 | 3/1993 | WIPO . |

*Primary Examiner*—Ronald Capossela
*Attorney, Agent, or Firm*—Renner, Otto, Boisselle & Sklar, P.L.L.

[57] ABSTRACT

A cryosurgical instrument comprises a cooling tip operable to be cooled by a flow of a cryogenic fluid within the tip; and a fluid transfer chamber having a fluid inlet for receiving cryogenic fluid, a first fluid outlet communicating with the cooling tip for supplying cryogenic fluid to the cooling tip, and a second fluid outlet communicating with an atmospheric air vent.

43 Claims, 5 Drawing Sheets

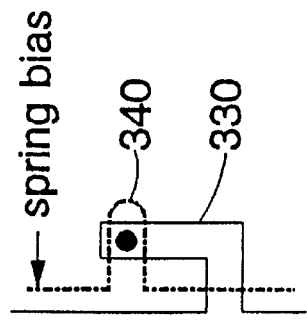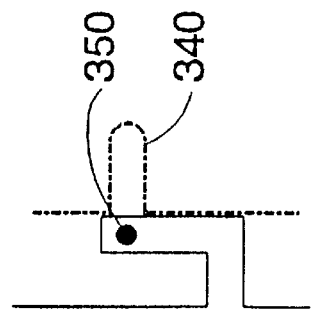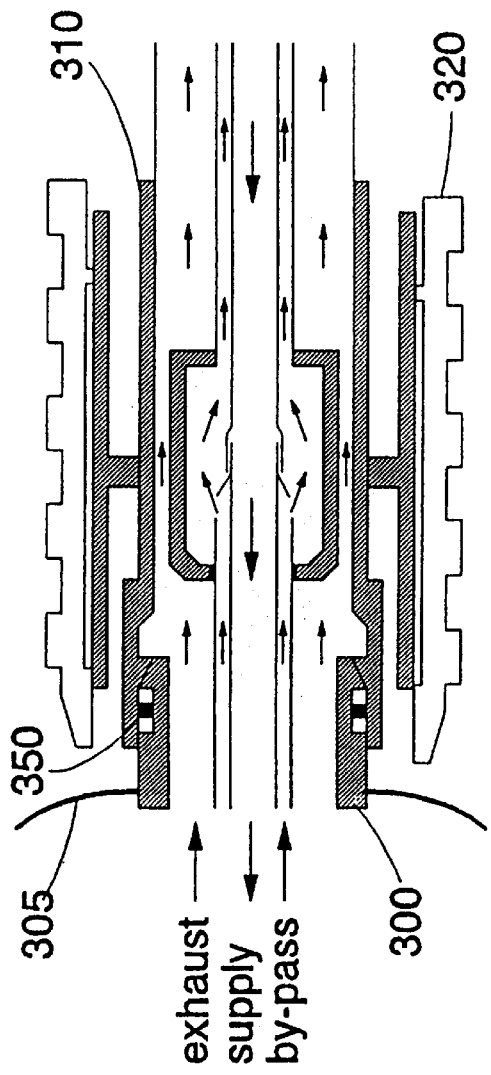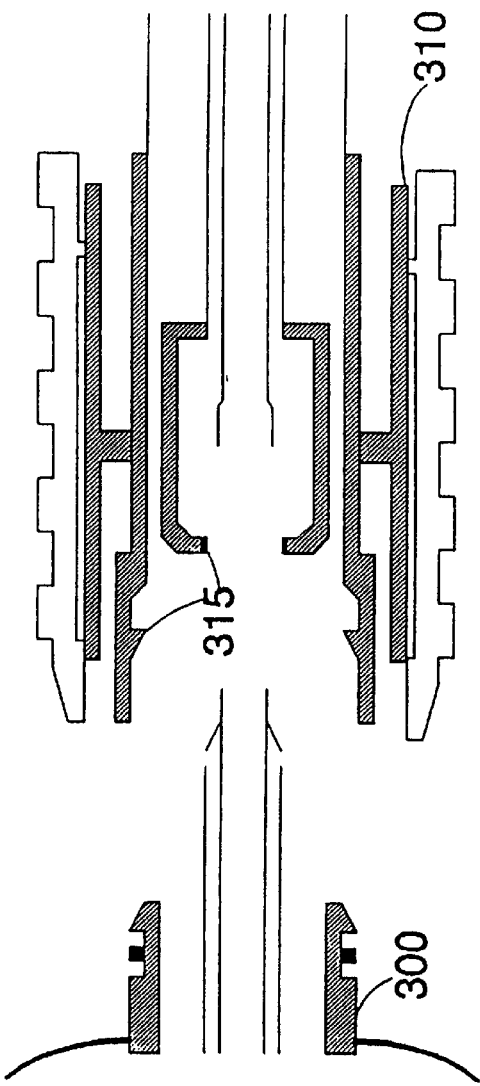

CRYOSURGICAL INSTRUMENT

This application is a continuation of International Patent Application No. PCT/GB95/00739 filed Mar. 31, 1995.

This invention relates to cryosurgical instruments.

It is known to use cryosurgical instruments in surgical operations in which living tissue is destroyed (or ablated) by cooling the tissue to well below the freezing point of water (e.g. −20° to −30° Centigrade).

A common form of a cryosurgical instrument for use in these surgical procedures comprises a hand-held cryosurgical probe, connected by various cryogenic fluid supply and exhaust conduits to a supply of cryogenic fluid such as a dewar vessel. A cooling tip of the probe is inserted into or touched against the tissue to be ablated and is then cooled by passing the cryogenic fluid into the interior of the cooling tip.

Often, the cryosurgical probe comprises a handle portion (for the surgeon or operator to hold) connected to the cooling tip by a relatively slender uncooled shaft. The purpose of the slender shaft is to allow the surgeon, when necessary, to insert the cooling tip deep into the tissue to be ablated or to manoeuvre the tip into a deep recess within the patient's body. Despite its potentially narrow cross section, the shaft carries at least a cryogenic fluid supply conduit for supplying cryogenic fluid to the cooling tip and an exhaust conduit for carrying cryogenic fluid from the cooling tip.

However, the very fact that the shaft has to be slender can cause problems with the flow of cryogenic fluid within the shaft, particularly along the supply conduit in a direction towards the cooling tip. This problem arises because the supply conduit has to be made narrow in order to fit into the shaft, and so a high cryogenic fluid velocity is required to force the fluid along the supply conduit. However, when the instrument is first used after a period of non-use, all of the conduits (including the supply conduit in the shaft) will tend to be warm. This can lead to localised boiling or expansion of the cryogenic fluid and it can be difficult to establish a flow rate of the cryogenic fluid towards the tip which is sufficient to cool the whole system down and to provide a high enough fluid velocity that the cryogenic fluid will pass along the slender shaft to reach the cooling tip.

WO 93/04647 discloses a cryosurgical instrument in which a metal tip of a cryosurgical probe is cooled by supplying liquid nitrogen to the interior of the tip. This instrument provides small vent holes to allow gas bubbles formed in the cryogenic fluid supply conduit to vent to an exhaust conduit before the bubbles reach the cooling tip.

This invention provides a cryosurgical instrument comprising: a cooling tip operable to be cooled by a flow of a cryogenic fluid within the tip; and a fluid transfer chamber having a fluid inlet for receiving cryogenic fluid, a first fluid outlet communicating with the cooling tip for supplying cryogenic fluid to the cooling tip, and a second fluid outlet communicating with an atmospheric air vent.

The invention addresses the problem of establish a sufficient flow rate of the cryogenic fluid towards the tip, particularly when the instrument is first used, by providing two possible return paths for the cryogenic fluid. Cryogenic fluid reaching the fluid transfer chamber can either pass through the first fluid outlet towards the cooling tip or can return to the atmospheric air vent via the second fluid outlet (which is preferably separate from an exhaust passage for fluid returning from cooling operation in the tip). This extra return path means that more fluid is passing along the various supply conduits towards the fluid transfer chamber, and so the fluid velocity is higher. This increased fluid velocity or flow rate can assist in forcing the fluid along a narrow conduit towards the cooling tip (if necessary) and can also help to cool the whole system down when the system is first used.

Preferably the instrument comprises a handle portion housing the fluid transfer chamber; and an elongate shaft linking the handle portion and the cooling tip. By housing the fluid transfer chamber in the handle portion, the extra fluid flow produced by this arrangement passes along all of the supply conduits leading to the handle portion.

In order to improve the proportion of the cryogenic fluid entering the fluid transfer chamber which then passes through the first fluid outlet, it is preferred that the fluid inlet and the first fluid outlet are disposed at opposite sides of the fluid transfer chamber. This proportion can further be improved in a preferred embodiment in which the fluid inlet is positioned to direct cryogenic fluid towards the first fluid outlet. In order to direct the fluid into the first fluid outlet, it is preferred that the interior of the fluid transfer chamber is tapered towards the first fluid outlet.

Preferably the fluid inlet and the second fluid outlet are disposed on the same side of the fluid transfer chamber. This can encourage gas bubbles formed in the supply conduit to vent via the second outlet, because the liquid's greater momentum will tend to cause the liquid to cross the chamber towards the first outlet. This can increase the proportion of liquid at the cooling tip, thus improving the cooling efficiency.

In order that fluid returning via the second fluid outlet to the atmospheric air vent can be used efficiently to cool the supply conduit carrying the fluid to the fluid transfer chamber, it is preferred that the instrument comprises an elongate supply conduit for supplying cryogenic fluid to the fluid inlet; and a by-pass return conduit substantially coaxial with the supply conduit for carrying cryogenic fluid from the second fluid outlet to the atmospheric air vent.

In order to avoid an unnecessary waste of cryogenic fluid when an appropriate flow rate has been established, the instrument preferably comprises a valve for controlling the flow of fluid through the atmospheric air vent. (In contrast, the apparatus of WO 93/04647 would in practice require a liquid scavenging system to recover cryogenic liquid exhausted through the vent holes).

Preferably the instrument comprises means for opening the valve to allow the flow of fluid through the atmospheric air vent for an initial predetermined period of use of the instrument.

It is preferred that the predetermined period is between about three minutes and about five minutes. After this time the flow of fluid through the second outlet can be completely or substantially stopped by the valve.

Since problems involving an insufficient fluid flow rate might arise after the predetermined period has elapsed, it is preferred that the instrument comprises means for detecting a flow rate of cryogenic fluid through the instrument; and means for opening the valve to allow the flow of fluid through the atmospheric air vent if the flow rate is less than a predetermined amount.

In order to avoid the potential hazard of liquid cryogenic fluid being vented directly to the atmosphere, it is preferred that the atmospheric air vent comprises a vented liquid trap chamber.

If any of the conduits used to transport the supply and exhaust cryogenic fluid become contaminated with moisture or debris, the performance of the instrument can suffer. In the case of particulate debris, problems can arise if the flow of cryogenic fluid to the tip is impeded. However, moisture ingress is a more serious problem, since any moisture present in the conduits when the instrument is first used can freeze and potentially block one of the conduits.

Accordingly, in a preferred embodiment, the instrument has an exhaust conduit for carrying cryogenic fluid from the tip to an exhaust atmospheric air vent; and means for directing a flow of substantially dry purging gas along at least a part of the exhaust conduit to exhaust through the atmospheric air vent.

This feature addresses the potential problem of moisture ingress into the system when cooling of the tip is not being performed, in particular through the exhaust vent, by maintaining a small but steady flow of purging gas out of the exhaust vent. This flow can be maintained when the system is not in use. In fact, preferably, the flow is only maintained when the system is not in use.

In order to avoid moisture ingress into the potentially very narrow fluid passages in the cooling tip, it is preferred that the directing means is also operable to direct the flow of gas through the cooling tip. This can also be advantageous in a re-usable probe, since some moisture can become trapped in the cooling tip during a steam sterilisation process. The purging gas can help to drive out this trapped moisture.

Preferably the directing means is operable to direct the flow of gas into the by-pass fluid return conduit (i.e. towards the second fluid outlet in the fluid transfer chamber, when the probe is not in cooling operation). This arrangement allows the fluid supply conduit to be sealed when the instrument is not in use, but still allowing the flow of purging gas to the interior of the tip.

The gas and the cryogenic fluid can conveniently be generated from the same source. This can give an added advantage that the steady flow of the purging gas can have a cooling effect on parts of the fluid supply such as a dip tube in a dewar vessel. It is therefore preferred that the instrument comprises a dewar vessel for storing a liquefied cryogenic fluid; and a dip tube extending into the fluid in the dewar vessel, the dip tube having a first passage for carrying cryogenic fluid for use in cooling the cooling tip, and a second passage for carrying gaseous cryogenic fluid into the third conduit. Since the purging gas is generated by gently boiling off liquid cryogenic fluid when the dewar is pressunsed, it is very dry indeed. It has been found that such extremely dry gas can actually tend to absorb moisture in the tubes.

In order to regulate the flow of the purging gas through the system, it is preferred that the instrument comprises a flow restricting valve in the path of the gas flow.

As an added safety feature, it is preferred that the instrument comprises means for detecting the pressure of the purging gas. Preferably the instrument also comprises means for inhibiting cooling operation of the instrument if the detected pressure is outside a predetermined range of gas pressures.

These safety features rely on detecting changes in pressure in the by-pass passages. When the system is not in use, with purging gas flowing along the by-pass passages, if the probe is not connected the gas pressure along those passages will be substantially atmospheric ($10^5$ Pa). When a correctly functioning probe is connected into the system, the gas pressure detected by the pressure detector will rise. If the probe is connected but has a blockage, the detected pressure will rise further.

Accordingly, the output of the pressure detector can be compared with a first threshold (e.g. $10^4$ Pa over atmospheric pressure, or alternatively $1.1 \times 10^5$ Pa), with cooling operation being inhibited if the detected pressure is below that threshold. A warning light could be illuminated on the control console to indicate that the probe is not connected. (This could be particularly useful in a multi-channel system where a probe could be connected to one of several fluid outlets; the system would prevent fluid being sent to an outlet when the probe was accidentally connected to another outlet).

Similarly, if the detected pressure exceeds another threshold (e.g. $2 \times 10^4$ Pa over atmospheric pressure or alternatively $1.2 \times 10^4$ Pa) then operation could again be inhibited, with a further warning light indicating a probe fault being illuminated.

Preferably the cryogenic fluid is liquid nitrogen and the gas is nitrogen gas.

When the instrument is used in a surgical procedure, the instrument has to be kept sterile to avoid the risk of infecting the patient during the procedure.

In use, the instrument has to be connected to a supply source of cryogenic fluid. It would not be feasible to sterilise the entire supply source and instrument combination, so the instrument is generally fitted with a connector to allow temporary connection of the instrument to the supply source during a surgical procedure. The instrument (and possibly, the connector) can then be sterilised before use.

A preferred embodiment of the invention provides connection apparatus comprising: complementary first and second connectors having cooperable locking means operable to lock the first connector to the second connector; in which: the first connector comprises means for activating the locking means to lock the first connector to the second connector; and the second connector comprises means for releasing the locking means to release the first connector from the second connector.

This feature recognises that two potentially conflicting requirements apply to connectors for use in sterile environments. First, the connector should be lockable to avoid the potentially hazardous possibility of the connector becoming detached from the supply source during the surgical procedure. However, if the locking mechanism requires a sterile operator or scrub nurse to touch the 'supply' (non-sterile) side of the connection, then that operator's hands can become contaminated with non-sterile contaminants. This means that the operator then has to go through a lengthy washing process and, in many cases, put on new sterile clothing and gloves before the operator can take a further part in the surgical procedure.

These apparently conflicting requirements are addressed by providing a connection apparatus in which two connectors can be locked together by a sterile operator holding only one of the connectors (the sterile connector). For security, the release mechanism is not mounted on the sterile connector. When it is time to release the connectors, the surgical procedure has been completed so a non-sterile operator can use the release means on the other (non-sterile) connector to release the locking of the connectors without concern over contamination with non-sterile material.

If the probe needs to be disconnected during a sterile procedure, for example to move the probe from one fluid supply to another in a multi-channel system, a sterile operator needs to operate the sterile side of the connector a non-sterile operator needs to release the other side of the connector. This dual-operator interlock can help prevent inappropriate disconnection of the probe during a procedure.

Preferably the first and second connectors comprise complementary bayonet locking formations.

In one preferred embodiment the second connector comprises a sleeve resiliently biased to overlie and prevent release of the bayonet locking formations, the first connector having sleeve displacing formations to displace the sleeve when the first and second connectors are locked together. In this way, the action of pushing the two connectors together displaces the sleeve to allow the bayonet to be locked. The sleeve then overlies the bayonet formations and prevents the two connectors being unlocked until the sleeve is moved by an operator.

In order to reduce further the risk of operator contamination, it is preferred that the first connector comprises guard formations for at least partially shielding an operator's hand when the first and second connectors are locked together.

Because the connectors are used to carry cryogenic fluids, it is preferred that the apparatus comprises a heater for heating at least one of the first connector and the second connector. The heater reduces the chance of moisture in or on the connector freezing and temporarily preventing the connector from being disconnected.

Viewed from a second aspect this invention provides a cryosurgical instrument comprising: a probe having a cooling tip operable to be cooled by a flow of a cryogenic fluid within the tip; means for providing a return path for cryogenic fluid from the probe without the fluid passing into the cooling tip; and means for preventing fluid flow via the return path after a predetermined period of operation of the instrument.

The invention will now be described by way of example with reference to the accompanying drawings, throughout which like parts are referred to by like references, and in which:

FIGS. 4a, 4b and 4c are schematic diagrams of a cryogenic fluid connector;

FIGS. 5a and 5b are schematic diagrams illustrating the operation of the cryogenic fluid connector of FIGS. 4a, 4b and 4c.

FIG. 1 is a schematic diagram of a cryosurgical probe system. The cryosurgical probe system is suitable for use in surgical operations in which living tissue is destroyed (or ablated) by cooling the tissue to well below the freezing point of water (e.g. −20° to −30° Centigrade).

Figure 1:
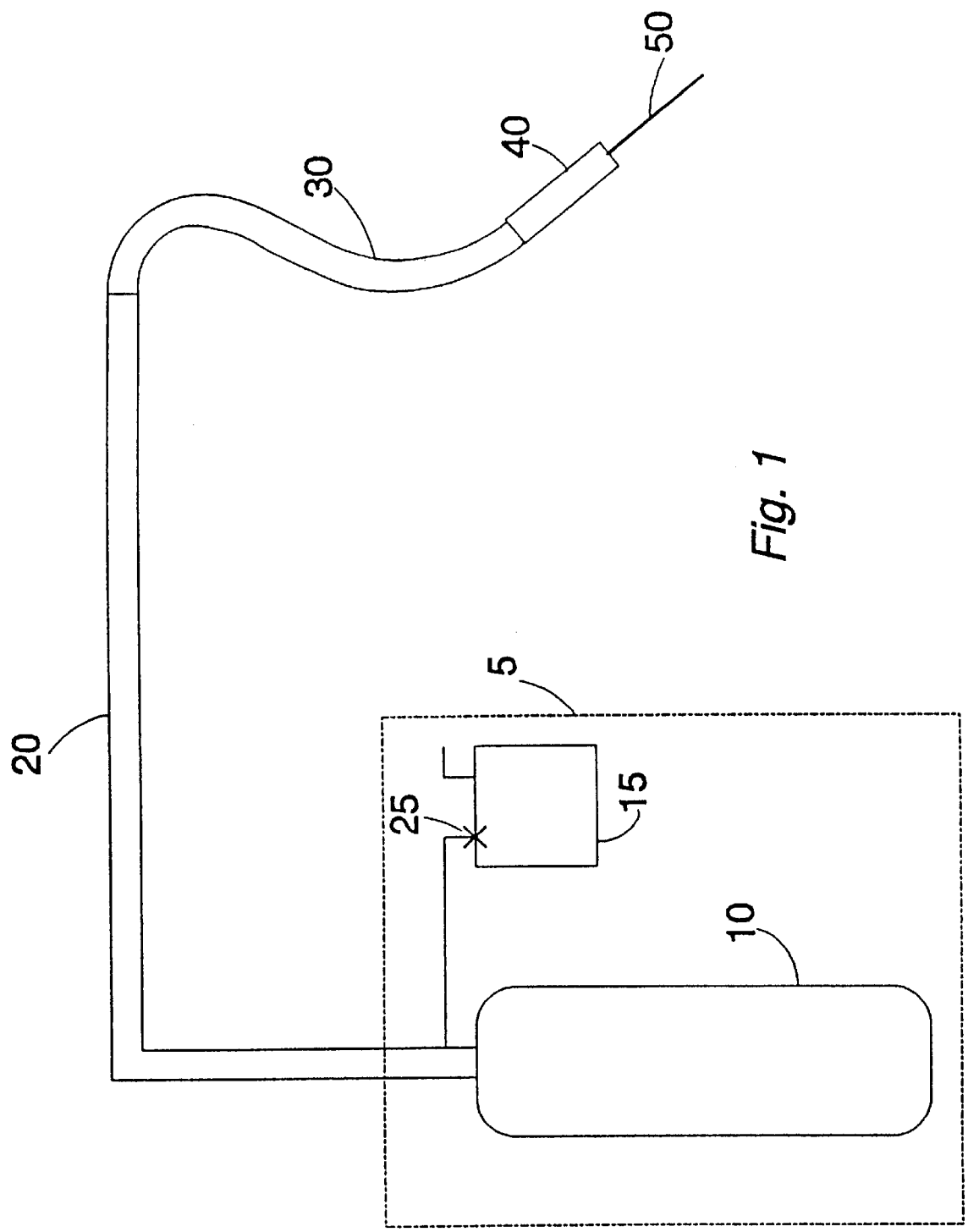
FIG. 1 is a schematic diagram of a cryosurgical probe system.

A cryogenic fluid, such as liquid nitrogen, is stored in a dewar vessel 10 forming part of a fluid supply apparatus 5. Alternative cryogenic fluids include freon 14, freon 22, freon 13, liquefied air and normally gaseous hydrocarbons (although inert fluids are preferred to flammable fluids).

The cryogenic fluid is supplied via an overhead connecting tube 20 and a flexible connecting tube 30 to a probe handle 40 and eventually to a probe tip 50. The flexible connecting tube 30 is linked to the overhead connecting tube 20 by a releasable connector (see FIGS. 4a, 4b, 4c, 5a and 5b). This allows the probe and flexible connecting tube to be steam sterilised for re-use.

The cryogenic supply apparatus 5 also has a by-pass exhaust chamber 15. This is a liquid trapping chamber vented to the atmosphere. Its role is to prevent the potentially hazardous direct venting of liquid nitrogen from a by-pass return path (described below) to the atmosphere. Entry into the chamber 15 is controlled by a by-pass valve 25 mounted on the chamber 15.

When the probe system is in use during a surgical operation in an operating theatre, the fluid supply apparatus 5 is placed a short distance away from an operating table or other support for the patient. The overhead connecting tube 20 allows the transfer of cryogenic fluid between the fluid supply apparatus 5 and the cryosurgical probe held by the surgeon, without obstructing the surgeon's access to the patient. The overhead connecting tube 20 may be a rigid structure in its own right, or may be a flexible or semi-flexible tube supported on a suitable supporting frame (not shown).

In use, the probe tip is inserted into bodily tissue to be destroyed (for example, a part of the patient's liver) and cryogenic fluid is supplied from the dewar vessel 10 to the interior of the probe tip 50. This causes the probe tip 50 to be cooled, which in turn cools the bodily tissue into which the probe tip 50 is inserted. Over a period of a few minutes, a volume of the bodily tissue surrounding the probe tip 50 is cooled to about −20° to −30° Centigrade, killing the cells in that volume of tissue. When the required volume of tissue has been cooled in this way, the probe tip 50 can be allowed to thaw, either through conduction of bodily heat from the patient or by passing a heated gas into the probe tip 50. The heated gas can be generated by passing gas from a gas storage cylinder (not shown) through an electric heating element (not shown). The probe tip is then withdrawn from the bodily tissue. If necessary, the procedure outlined above may be repeated a number of times at different locations in the body or in a particular organ if a particularly large volume of tissue is to be destroyed.

The cryogenic fluid remains inside the probe tip 50 during the cooling process. In other words there is no potentially dangerous contact between the cryogenic fluid and the patient's bodily tissue.

Figure 2:
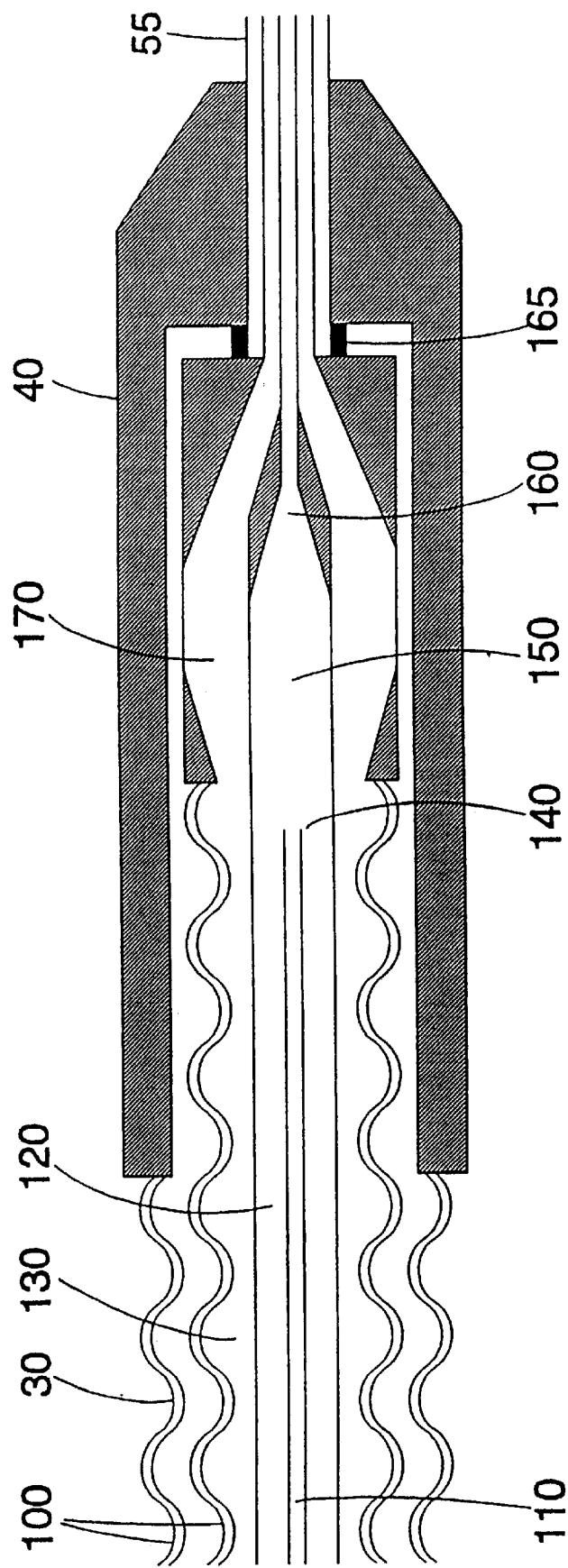
FIG. 2 is a schematic diagram of a cryosurgical probe handle.
Figure 3A:
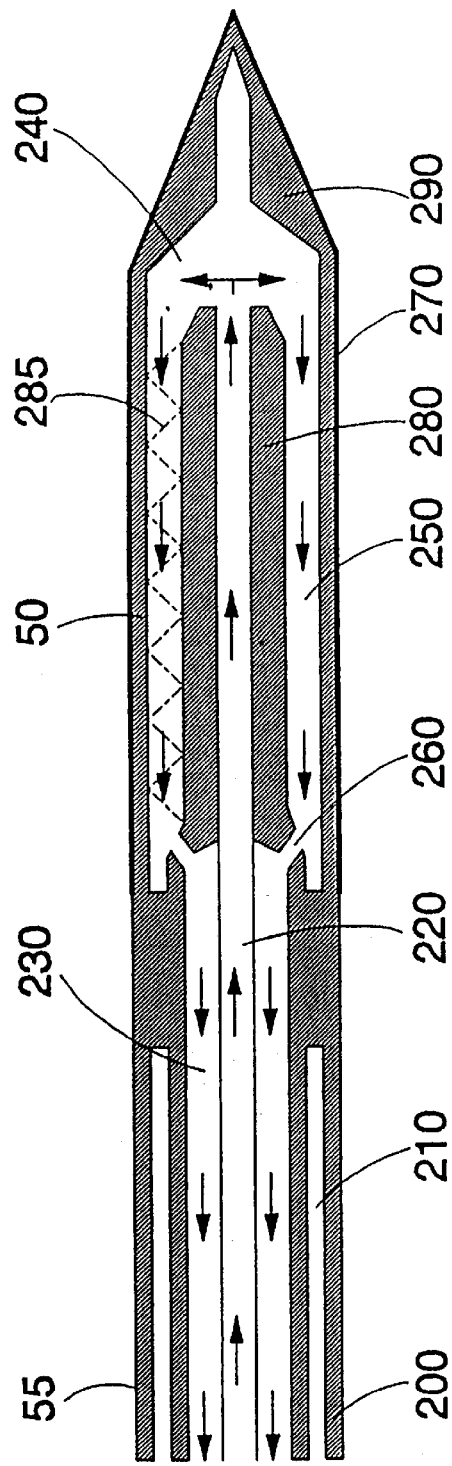
FIGS. 3a and 3b are enlarged schematic diagrams of a cryosurgical probe tip.
Figure 3B:
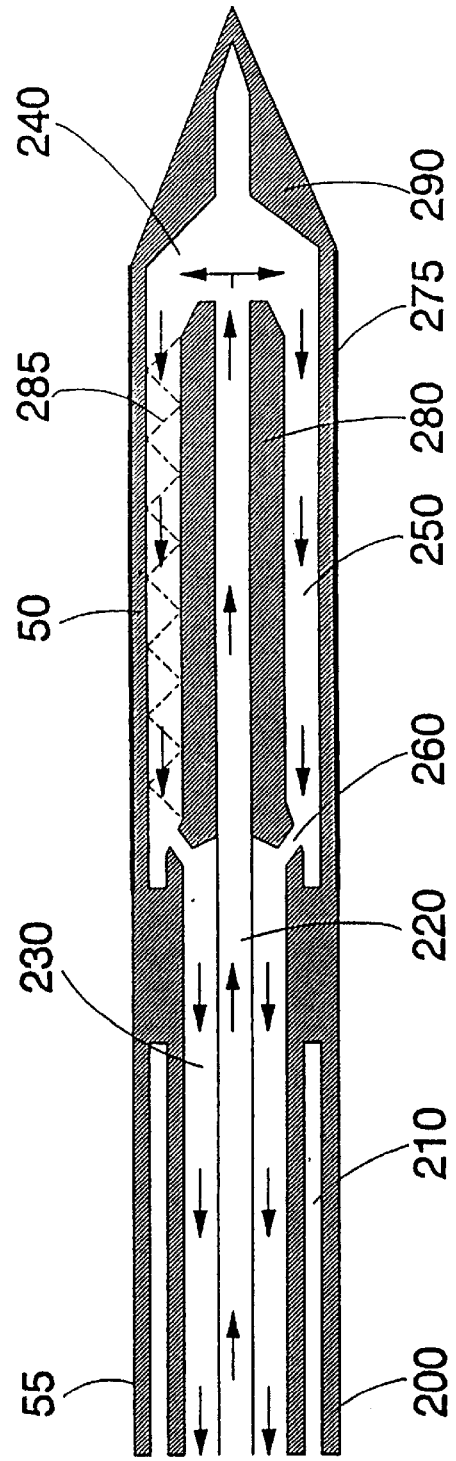

FIG. 2 is a schematic diagram of the probe handle 40, and FIGS. 3a and 3b are enlarged schematic diagrams of the cryosurgical probe tip 50.

Referring to FIGS. 2 and 3a, the probe handle 40 is connected to the flexible connecting tube 30 for the supply and exhaust of cryogenic fluid. The flexible connecting tube 30 is in fact a coaxial structure of several tubes. At the outside of the flexible connecting tube 30 are two skins 100, each formed of a double-walled structure of flexible corrugated tubing. This double-skinned structure provides good heat insulation to prevent the outside of the flexible connecting tube 30 becoming hazardously cold when the probe is in use. Inside the inner skin 100 are two coaxial PTFE (polytetrafluoroethane) tubes, namely a cryogenic fluid supply tube 110 and, surrounding the cryogenic supply tube 110, a by-pass tube 120. A region 130 between the outside of the by-pass tube 120 and the inner skin 100 forms an exhaust gas passage. Seals 165 are provided to terminate the annular space between the skins 100.

Cryogenic fluid supplied through the fluid supply tube 110 emerges at high velocity through a fluid outlet 140. The fluid emerges into a transfer chamber 150, from which some of the fluid may return towards the fluid supply apparatus along the by-pass tube 120, and some may pass through a convergent nozzle 160 in a direction towards the probe tip 50.

For the first few minutes of operation of the probe system, the by-pass tube 120 is connected via the by-pass valve 25 (to be described below) to an atmospheric air vent. This means that a significant proportion of the cryogenic liquid emerging from the fluid outlet 140 is able to return along the by-pass tube 120.

This arrangement means that the flow rate or fluid velocity of cryogenic fluid emerging from the outlet 140 can be increased by allowing some of the fluid to vent via the by-pass tube 120. The need for this arises because the fluid passing through the convergent nozzle 160 has to pass along a narrow fluid supply passage towards the tip 50. If the fluid velocity is increased by using the by-pass tube and valve, the initial flow of cryogenic fluid along the narrow fluid supply passage can be made much more reliable.

In addition, the by-pass system allows bubbles of gas formed in the fluid supply tube 110 to escape through the by-pass path, rather than passing the gas through the cooling tip 50. This diversion of the gas bubbles away from the tip can assist in cooling the tip down during the early stages of operation, since the cryogenic fluid has a much higher heat capacity per unit volume in liquid form than in gaseous form.

The separation of gas and liquid cryogenic fluid in the chamber 150 is helped by the relative positioning of the fluid outlet 140, the convergent nozzle 160 and the entrance to the by-pass tube 120. In a stream of gas and liquid cryogenic fluid, the liquid will have a much greater momentum than the gas, because it is about 600 times more dense than the gas phase. This means that the liquid is more likely to continue across the chamber 150 from the outlet 140 into the convergent nozzle 160, whereas the gas is more likely not to cross the chamber 150. The by-pass tube is connected to an atmospheric air vent and so provides a low-pressure, wide bore path for the gas to escape, whereas the convergent nozzle leads to a narrower bore, higher pressure path. Accordingly, the gas tends to follow the by-pass path.

The by-pass passages throughout the system are coaxial, surrounding the fluid supply tubes. This means that during the initial period of operation when the by-pass valve 25 is open, the fluid supply tubes are cooled by the flow of cryogenic fluid along the by-pass passages. Cooling the supply tubes is important to allow the cryogenic fluid to reach the probe tip 50 while still in liquid form (for efficient cooling of the probe tip 50), rather than as a gas.

After a predetermined time period in operation (e.g. 3 to 5 minutes) a control circuit (not shown) closes the by-pass valve 25 and so prevents further flow of cryogenic fluid along the by-pass tube 120. After this period in operation, the narrow fluid supply passage is full of the cryogenic fluid and is sufficiently cool that further fluid can flow easily down the passage. This means that the by-pass path is no longer needed, so it is shut off to avoid an unnecessary waste of the cryogenic fluid.

The by-pass valve 25 can also be. controlled in response to the flow rate of exhaust fluid from the probe tip 50. If a problem arises which cuts down the flow of cryogenic fluid into the probe tip 50, this can be detected as a drop in the exhaust flow rate below a threshold rate, by means of a suitable flow rate detector (not shown). In order to increase the fluid flow to the probe tip 50, the by-pass valve 25 can then be opened, either for a predetermined time or until the exhaust flow rate reaches the threshold rate. As described above, this has the effect of increasing the fluid velocity as the fluid approaches the convergent nozzle 160, and so increasing the fluid flow rate into the probe tip 50.

During operation when the by-pass valve is closed, the consumption of cryosurgical fluid by the probe tip 50 is about 0.25 liters per minute.

Exhaust fluid emerging from the tip 50 passes into a coaxial exhaust chamber 170 which communicates with the exhaust passage 130.

FIG. 3a is an enlarged schematic diagram of the probe tip 50. The probe tip 50 is connected to the handle 40 by a probe shaft 55. The probe shaft 55 has an outer wall 200 made of silver which surrounds a coaxial vacuum chamber 210. The vacuum chamber 210 provides a degree of heat insulation between the cryogenic fluid passing inside the shaft 55 and the bodily tissue in contact with the shaft 55. This means that the freezing effect takes place primarily at the tip of the probe tip 50, rather than along the shaft 55, thus giving the surgeon better control over the location to be frozen. Within the shaft 55, there is a coaxial structure of a PTFE supply tube 220 and a surrounding exhaust passage 230. The returning exhaust fluid along the exhaust passage 230 can help to keep the incoming fluid cool.

The supply tube 220 continues as far as a heatsink 280 which then carries the cryogenic fluid to a chamber 240. The chamber 240 communicates with exhaust passages 250. Exhaust fluid passing through the exhaust passages 150 flows into the exhaust passage 230 through a series of spaced exhaust apertures 260. The path of fluid into the tip 50 and back along the exhaust passage 230 is shown schematically in FIGS. 2 and 3a using direction arrows.

When the cryogenic fluid emerges into chamber 240, it starts to boil. There are two possible modes of boiling which can take place. If so-called 'film' boiling occurs, a film of nitrogen gas forms between the inner surface of the chamber 240 and the boiling liquid nitrogen. This film of gas reduces the heat conduction between the boiling liquid and the silver body of the tip 50 and thus reduces the cooling efficiency of the probe. The other possible mode of boiling is referred to as 'nucleate' boiling. In this mode boiling takes place at discrete bubble-forming sitcs at the liquid-solid boundary. The film of gas does not form, so the heat conduction between the boiling liquid and the outer silver body of the tip 50 is much better, and the cooling efficiency of the tip is thus improved.

It has been found that, unexpectedly, the nucleate boiling process can be encouraged by providing a thermally insulating coating on at least a part of the outer surface of the tip 50.

In the embodiment shown in FIG. 3a, a thin PTFE coating 270 on the entire outer surface of the tip 50 is used. The coating is about 10 to $20 \times 10^{-6}$ meters thick (preferably less than about $30 \times 10^{-6}$ meters thick).

In an alternative embodiment shown schematically in FIG. 3b, a similar insulating coating 275 is applied to a "boiling" region of the tip. This region is a part of the tip in which the liquid tends to boil, namely the passages along the milled flats of the screw-threaded connection 285. In this boiling region, the cryogenic liquid is in close thermal contact with tissue surrounding the tip, which contrasts with the insulated supply and exhaust passages 220, 230, where the liquid is relatively thermally isolated from ambient conditions. It has been found that coating the circumference of the tip over substantially this boiling region encourages the nucleate boiling referred to above.

Another factor which has been found to increase the likelihood of nucleate rather than film boiling is the construction of the cooling tip 50. Before the cryogenic fluid reaches the chamber 240, it passes inside the heatsink 280. (Before reaching the heatsink 280, the fluid was passing along the heat-insulating PTFE supply tube 220). The heatsink 280 is made of silver and is thermally connected by a screw thread connection (shown schematically as 285) to the outer silver casing 290 of the cooling tip. Longitudinal flats are milled on the heat sink 280 to form the exhaust passages 250. This technique of passing the cryogenic fluid either side of a hcatsink thermally connected to the outer wall of the cooling tip 50 has been found to promote nucleate rather than film boiling within the cooling tip.

The outer silver wall 200 of the probe shaft 55 has a number of beneficial effects. It is in thermal contact with both the patient's tissue and the tip 50, and so it can conduct body heat towards the tip 50 to assist in defrosting the tip 50. It can act as a heat sink to help the shaft remain unfrozen even when the tip 50 is cooled. Also, the silver material helps to prevent corrosion of the shaft 55. This is important in a re-usable device.

FIGS. 4a, 4b and 4c are schematic diagrams of a cryogenic fluid connector. The connector is formed of two complementary connectors, a first connector 300 linked to the flexible connecting tube 30 and a second connector 310 linked to the overhead connecting tube 20. FIG. 4a shows the first and second connectors mated together, FIG. 4b shows the first connector and FIG. 4c shows the second connector.

In FIG. 4a, the path of fluid flow in the supply, by-pass and exhaust passages is indicated by arrows.

The connectors are locked together by a bayonet fixing formed by pins (350) on the first connector engaging in angled bayonet slots (not shown on FIGS. 4a, 4b and 4c) in the second connector. The two connectors are thus linked together by pushing the first connector into the second connector, and then twisting the first connector with respect to the second connector.

Sealing rings are provided at the mating surfaces 315 of the connectors.

The connector 310 has a resiliently biased sleeve 320 which overlies the bayonet connection and prevents the connection being disconnected. The operation of the sleeve 320 is illustrated in FIGS. 5a and 5b.

FIGS. 5a and 5b are schematic diagrams showing a bayonet slot 330 in the second connector, a retaining slot 340 formed by or connected to the sleeve 320, and a bayonet pin 350 of the first connector. (For clarity of FIGS. 4a to 4c, the retaining slot 340 has not been shown in these Figures. The retaining slot could be formed in the actual sleeve itself, or in a plate or other member attached to the sleeve).

When the pin 350 is pushed into the opening of the slot 330, it pushes against the spring-biased sleeve 320 until the pin has reached the bottom of the slot 330. The pin can then slide along the slot 330 during the rotational movement of the first and second connectors. During this movement the sleeve 320 is held back against the spring bias. However, when the pin reaches the retaining slot 340, the sleeve can return to its rest position and the pin is retained by the combination of the slot 330 and the retaining slot 340. The pin is no longer free to rotate, and so is captive between the slot 330 and the slot 340. This situation is shown in FIG. 5a.

Accordingly, to lock the connector as shown in FIG. 5a, it is necessary for an operator to touch only the first connector 300. If this connector has been sterilised then a sterile operator or 'scrub nurse' can safely lock the two connectors together without having to touch the second (non-sterile) connector 310.

A flange 305 is provided to shield the operator's hand from accidentally touching the second connector during the connection process.

In order to unlock the two connectors, the sleeve 320 must be manually pushed against the spring bias into a position shown in FIG. 5b. At this stage the surgical procedure is over, so it is safe for a (non-sterile) operator to touch the sleeve 320. Once the sleeve has been pushed back, the first connector can be rotated and withdrawn to free the pin 350 from the slot 330. The sleeve is made of a plastics material, to reduce the danger of the sleeve freezing to the operator's hand when touched.

The connector 310 incorporates an electric heater (not shown), which is energised at least during the time when the cryogenic fluid is passed through the connector. The heater reduces the chance of moisture in or on the connector freezing and temporarily preventing the connector from being disconnected.

Figure 6:
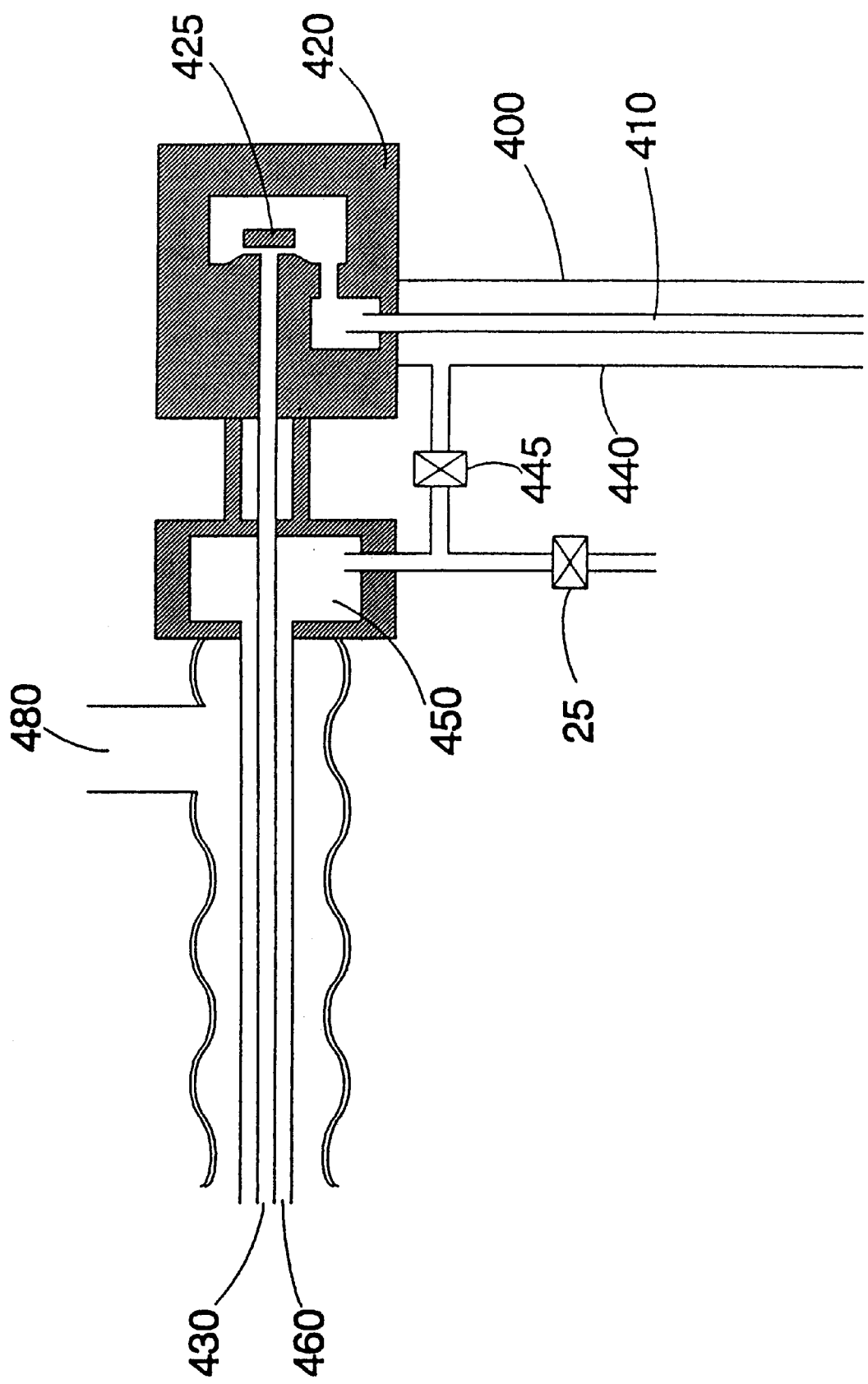
FIG. 6 is a schematic diagram of a cryogenic fluid supply apparatus.

FIG. 6 is a schematic diagram of part of the cryogenic fluid supply apparatus 5 of FIG. 1.

A dip tube 400 extends into the dewar vessel 10, to a level below the level of the cryogenic fluid in the dewar vessel. In normal operation, the cryogenic fluid to be supplied to the probe tip 50 passes along an axial supply passage 410, into the interior of a valve 420, and from the valve 420 into the axial supply passage 430 of the overhead connecting tube 20. The valve 420 can be opened and closed by means of a solenoid controlled ruby or PTFE seal 425.

A second outlet from the dewar vessel is also provided, along an outer coaxial passage 440 in the dip tube 400. During quiescent operation when the dewar vessel is pressurised but the cooling tip is not being cooled (i.e. cryogenic liquid is not being supplied to the tip), this outlet provides a purging flow of cool gas through the various connecting tubes, the probe tip 50, and the exhaust passages of the cryosurgical probe system. The purging gas is actually generated by the liquid nitrogen in the dewar vessel boiling very gently.

The passage 440 is connected, via a flow restricting valve 445, to a chamber 450 which communicates with the by-pass return path 460 from the probe handle 40.

The by-pass valve 25 selectively vents or blocks fluid output from the chamber 450, as described above. When the probe system is not in use, the by-pass valve is closed and so purging gas flows at a low flow rate into the chamber 450 and then along the by-pass passages towards the probe handle 40 (i.e. in the opposite direction to the direction in which cryosurgical fluid flows along the by-pass passages when the by-pass valve is open). When the purging gas reaches the probe handle 40, it passes along the supply tube 220 of the probe shaft 55 to the probe tip 50 and then returns along the exhaust passages towards the fluid supply apparatus. The exhaust passages communicate with an exhaust vent 480 at the fluid supply apparatus.

The purging gas serves three main purposes. First, it can help to prevent the ingress of moisture into the system (in particular, through the exhaust vent 480), by maintaining a small but steady flow of gas out of the exhaust vent 480. Second, the small flow along the dip tube 400 can help to keep the dip tube cool, thus reducing the cool down time when the system is first used. Third, in a re-usable probe some moisture can become trapped in the cooling tip during a steam sterilisation process. The purging gas can help to drive out this trapped moisture. Since the purging gas is generated by boiling off liquid nitrogen, it is very dry indeed. It has been found that such extremely dry gas can actually tend to absorb moisture in the tubes.

A further use of the purging gas is obtained by placing a pressure sensor (not shown) to measure gas pressure along the by-pass passages, at any point between the gas outlet of the flow restricting valve 445 and the connector 310 (linked to the overhead connecting tube). For example, the pressure sensor could be connected to communicate with the chamber 450.

This pressure detector has two roles. It can be used to detect whether the probe is connected at the connector 310, as a safety feature to prevent cooling operation of the system being started without a probe in place to receive the cryogenic fluid. As an additional safety feature, the pressure detector can be used to detect blockages or malfunctions in the fluid passageways, before cooling operation is initiated.

These safety features rely on detecting changes in pressure in the by-pass passages. When the system is not in use, with purging gas flowing along the by-pass passages, if the probe is not connected the gas pressure along those passages will be substantially atmospheric ($10^5$ Pa). When a correctly functioning probe is connected into the system, the gas pressure detected by the pressure detector will rise. For example, in a prototype of the present embodiment, the pressure in the by-pass passageways rises by about 100 millibars ($10^4$ Pa) when a correctly functioning probe is connected. If the probe is connected but has a blockage, the detected pressure will rise further.

Accordingly, the output of the pressure detector can be compared with a first threshold (e.g. $10^4$ Pa over atmospheric pressure, or alternatively $1.1 \times 10^5$ Pa), with cooling operation being inhibited if the detected pressure is below that threshold. A warning light (not shown) could be illuminated on the control console to indicate that the probe is not connected. (This could be particularly useful in a multichannel system where a probe could be connected to one of several fluid outlets; the system would prevent fluid being sent to an outlet when the probe was accidentally connected to another outlet).

Similarly, if the detected pressure exceeds another threshold (e.g. $2 \times 10^4$ Pa over atmospheric pressure or alternatively $1.2 \times 10^4$ Pa) then operation could again be inhibited, with a further warning light (not shown) indicating a probe fault being illuminated.

We claim:

1. A liquid cryogen operated cryosurgical probe comprising:
   a cooling tip having an expansion region in which liquid cryogen vaporizes to cool the tip;
   a cryogen inlet;
   a first cryogen outlet;
   a second cryogen outlet;
   a first fluid flow path in the probe from the inlet through the expansion region in the tip to the first cryogen outlet; and
   a second bypass flow path in the probe from the inlet and by-passing the cooling tip, the second flow path leading to the second cryogen outlet.

2. A probe according to claim 1, comprising a fluid transfer chamber from which the first and second flow paths branch.

3. A probe according to claim 2, wherein the fluid transfer chamber comprises a chamber inlet port, and the chamber has a greater transverse dimension than the chamber inlet port.

4. A liquid cryogen operated cryosurgical apparatus, comprising:
   (a) a probe comprising:
      a cooling tip with an expansion region in which liquid cryogen vaporizes to cool the tip;
      a cryogen intlet;
      a first cryogen outlet;
      a second cryogen outlet;
      a first fluid flow path in the probe from the inlet through the expansion region in the tip to the first cryogen outlet; and
      a second bypass flow path in the probe from the inlet and by-passing the cooling tip, the second flow path leading to the second cryogen outlet;
   (b) a supply of liquid cryogen;
   (c) a first conduit coupled between the supply of liquid cryogen and the inlet of the probe;
   (d) a second conduit coupled to the first outlet of the probe for exhausting vaporized cryogen; and
   (e) a third conduit coupled to the second outlet of the probe for exhausting cryogen flowing in the bypass path.

5. Apparatus according to claim 4, wherein the first, second and third conduits are separate conduit channels in a multichannel tube.

6. Apparatus according to claim 4, further comprising a control valve for controlling the flow through the second path in the probe.

7. Apparatus according to claim 6, wherein the valve is coupled to the third conduit.

8. Apparatus according to claim 6, comprising a control unit for opening the valve to allow the flow of fluid through the return path for an initial predetermined period of use of the instrument.

9. Apparatus according to claim 8, in which the predetermined period is between about three minutes and about five minutes.

10. Apparatus according to claim 6, comprising a flow sensor for detecting a flow rate of cryogenic fluid through the probe; and a control unit for opening the valve to allow the flow of fluid through the return path if the flow rate is less than a predetermined amount.

11. Apparatus according to claim 4, in which the third conduit leads to a vented liquid trap chamber.

12. A liquid cryogen operated cryosurgical apparatus comprising:
   a probe having a cooling tip which is cooled by vaporization of liquid cryogen flowing within the tip,
   a first flow path for cryogen fluid, the first flow path extending in the probe through the tip;
   a second return flow path for cryogen fluid, the second flow path extending in the probe and bypassing the tip; and
   a valve for controlling the flow of cryogenic fluid in the second flow path;
   wherein when the valve is in a first state, cryogen fluid is permitted to flow in the second flow path thereby to increase the rate of cryogen flow into the probe, and when the valve is in a second state, the flow of cryogen fluid in the second path is blocked.

13. Apparatus according to claim 12, wherein the valve is remote from the probe.

14. Apparatus according to claim 12, wherein the valve is open in said first state, and the valve is closed in said second state.

15. Apparatus according to claim 12, comprising a controller for opening the valve to allow the flow of fluid through the return path for an initial predetermined period of use of the instrument.

16. Apparatus according to claim 12, in which the predetermined period is between about three minutes and about five minutes.

17. Apparatus according to claim 12, comprising a flow rate detector for detecting a flow rate of cryogenic fluid through the probe; and a device for opening the valve to allow the flow of fluid through the return path if the flow rate is less than a predetermined amount.

18. Apparatus according to claim 12, in which second flow path leads to a vented liquid trap chamber.

19. Apparatus according to claim 12, wherein the probe comprises:

a cryogen fluid inlet conduit; and a fluid transfer chamber into which the inlet conduit opens at a fluid inlet, the transfer chamber having a first outlet communicating with a first flow path through the cooling tip for liquid cryogen, and a second outlet communicating with the return path from the probe.

20. Apparatus according to claim 19, wherein the transfer chamber defines a region wider than the inlet thereto.

21. Apparatus according to claim 19, wherein the probe comprises:

a handle portion housing the fluid transfer chamber; and an elongate shaft linking the handle portion and the cooling tip.

22. Apparatus according to claim 19, in which the fluid inlet and the first fluid outlet are disposed at opposite sides of the fluid transfer chamber.

23. Apparatus according to claim 22, in which the fluid inlet is positioned to direct cryogenic fluid towards the first fluid outlet.

24. Apparatus according to claim 23, in which the interior of the fluid transfer chamber is tapered towards the first fluid outlet.

25. Apparatus according to claim 19, in which the fluid inlet and the second fluid outlet are disposed on the same side of the fluid transfer chamber.

26. Apparatus according to claim 12, comprising an elongate supply conduit for supplying cryogenic fluid to the probe; and a return conduit substantially coaxial with the supply conduit for carrying cryogenic fluid along the return path from the probe.

27. Apparatus according to claim 12, comprising:

an exhaust conduit for carrying cryogenic fluid along the exhaust path from the tip to an exhaust atmospheric air vent; and means for directing a flow of substantially dry purging gas along at least a part of the exhaust conduit to exhaust through the exhaust atmospheric air vent.

28. Apparatus according to claim 27, in which the directing means is operable to direct the flow of gas through the cooling tip.

29. Apparatus according to claim 28, in which the directing means is operable to direct the flow of gas into the fluid return conduit.

30. Apparatus according claim 27, comprising:

a dewar vessel for storing a liquefied cryogenic fluid; and a dip tube extending into the fluid in the dewar vessel, the dip tube having a first passage for carrying cryogenic fluid for use in cooling the cooling tip, and a second passage for carrying gaseous cryogenic fluid into the fluid return conduit.

31. Apparatus according to claim 30, comprising a flow restricting valve in the path of the gas flow.

32. Apparatus according to claim 27, comprising means for detecting the pressure of the purging gas.

33. Apparatus according to claim 32, comprising means for inhibiting cooling operation of the instrument if the detected pressure is outside a predetermined range of gas pressures.

34. Apparatus according to claim 32, comprising cryogenic fluid conduit connection apparatus having complementary first and second connectors having cooperative locking means operable to lock the first connector to the second connector; in which:

the first connector comprises means for activating the locking means to lock the first connector to the second connector; and the second connector comprises means for releasing the locking means to release the first connector from the second connector.

35. Apparatus according to claim 34, in which the first and second connectors comprise at least fluid supply and fluid exhaust conduits, corresponding fluid conduits in the first and second connectors being arranged to mate when the first and second connectors are locked together.

36. Apparatus according to claim 34, in which the first and second connectors comprise complementary bayonet locking formations.

37. Apparatus according to claim 36, in which the second connector comprises a sleeve resiliently biased to overlie and prevent release of the bayonet locking formations, the first connector having sleeve displacing formations to displace the sleeve when the first and second connectors are locked together.

38. Apparatus according to claim 37, in which the first connector comprises guard formations for at least partially shielding an operator's hand when the first and second connectors are locked together.

39. Apparatus according to claim 34, comprising a heater for heating at least one of the first connector and the second connector.

40. Apparatus according to claim 12, in which the cryogen fluid is liquid nitrogen.

41. A liquid cryogen operated cryosurgical instrument, comprising:

a cooling tip which is cooled by vaporization of liquid cryogen within the tip;

a cryogen fluid inlet conduit; and a fluid transfer chamber into which the inlet conduit opens at a fluid inlet, the transfer chamber defining a region wider than the inlet conduit, and having a first outlet communicating with a first flow path through the cooling tip for liquid cryogen, and a second outlet communicating with a second flow path without passing into the cooling tip.

42. An instrument according to claim 41, wherein the instrument is a cryosurgical probe.

43. A cryosurgical instrument comprising:

a probe having a cooling tip operable to be cooled by a flow of a cryogenic fluid within the tip;

means for providing a return path for cryogenic fluid from the probe without the fluid passing into the cooling tip; and means for preventing fluid flow via the return path after a predetermined period of operation of the instrument.

* * * * *